United States Patent [19]

Pedotti

[11] Patent Number: 4,598,717
[45] Date of Patent: Jul. 8, 1986

[54] APPARATUS FOR CLINICALLY DOCUMENTING POSTURAL VICES AND QUANTIFYING LOADS ON BODY SEGMENTS IN STATIC AND DYNAMIC CONDITIONS

[75] Inventor: Antonio Pedotti, Brenta, Italy

[73] Assignee: Fondazione Pro Juventute Don Carlo Gnocchi, Milan, Italy

[21] Appl. No.: 616,876

[22] Filed: Jun. 4, 1984

[30] Foreign Application Priority Data

Jun. 10, 1983 [IT]  Italy ............................ 21559 A/83

[51] Int. Cl.$^4$ ............................................... A61B 5/10
[52] U.S. Cl. .................................................. 128/779
[58] Field of Search ............... 128/774, 779, 781, 782

[56] References Cited

U.S. PATENT DOCUMENTS

| | | |
|---|---|---|
| 3,872,443 | 3/1975 | Ott . |
| 3,894,437 | 7/1975 | Hagy et al. ........................ 128/779 |
| 4,122,840 | 10/1978 | Tsuchiya et al. .................... 128/779 |
| 4,136,682 | 1/1979 | Pedotti ................................ 128/779 |
| 4,267,728 | 5/1981 | Manley et al. ...................... 128/779 |

FOREIGN PATENT DOCUMENTS 1178121  1/1970  United Kingdom ................ 128/779

OTHER PUBLICATIONS

"An Outstanding Tool in Biomechanics", Kistler, Aug. 1974.
"Measuring Man's Stability of Stance", Journal of Clinical Engineering, Terekloo, Mar. 1979.

Primary Examiner—Edward M. Coven
Assistant Examiner—Max F. Hindenburg
Attorney, Agent, or Firm—Guido Modiano; Albert Josif

[57] ABSTRACT

The apparatus comprises a platform for supporting a patient to be examined and providing at least one component of the force exerted thereon by the patient, a TV camera so positioned as to pick up the image of the patient on the platform and cooperating with a monitor for displaying the picked up image in the form of a vectorial representation under the control of image processing circuitry and of a processor unit.

6 Claims, 4 Drawing Figures

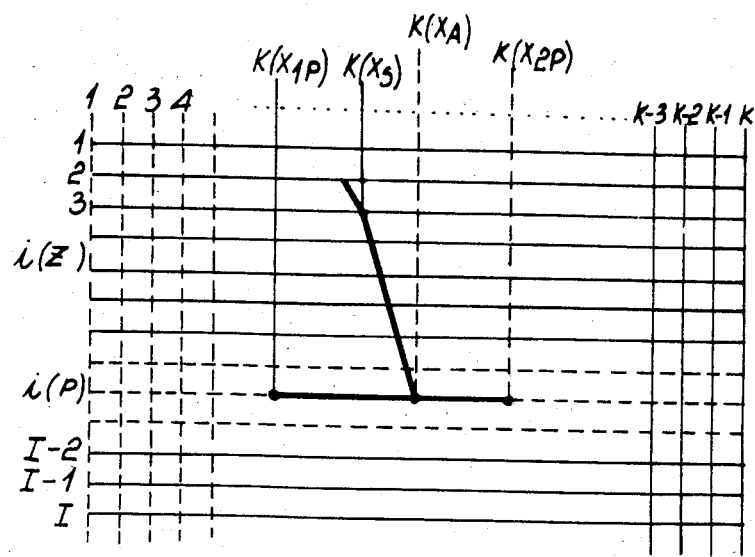
Fig. 3
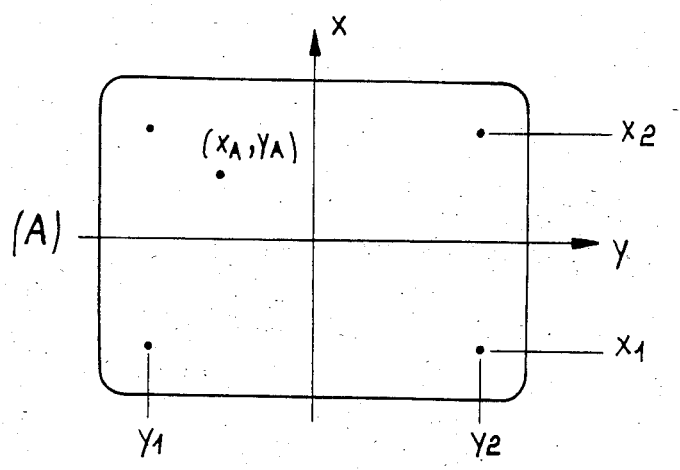
Fig. 4
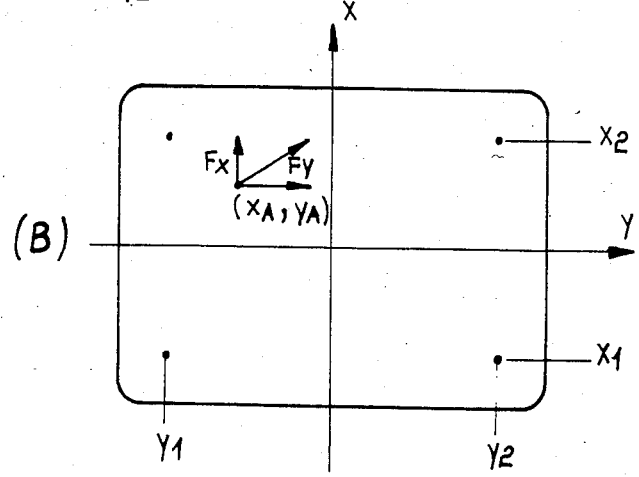

APPARATUS FOR CLINICALLY DOCUMENTING POSTURAL VICES AND QUANTIFYING LOADS ON BODY SEGMENTS IN STATIC AND DYNAMIC CONDITIONS

BACKGROUND OF THE INVENTION

This invention relates to an apparatus for clinically documenting postural vices, adapted to provide monitoring of scoliotic risk subjects, as well as differential diagnosis, prognosis, and therapeutic stage control of scoliosis and various pathologies of the spine.

As is known, scoliosis is a permanent deformation of the rachis, which is brought forward by a pathologic bend of the spine in the front plane. Scoliotic attitudes are apparent in about 15% of children, mainly in school age. Of these, about 3% harbor an evolutive scoliosis which materializes in a scoliosis of some import (idiopathic scoliosis) requiring cruentous or incruental clinic treatment. Thus, the need arises from this situation for a large scale screening method for timely diagnosticating such affections, as well as for methods of checking a subject for timely outlining a possible evolution of the disease.

For all these analyses, it is current practice to use rachis radiography which, as is known, present more than negligible elements of toxicity.

Like arguments apply to therapeutic intervention, which in most cases of evolutive scoliosis requires the use of corsets and corrective gymnastics. These are, unfortunately, long term (on the order of some years) interventions which must be supported by constant documentation of the rachis state, also by radiography. Thus, on the one hand, the doctor requires continued documentation of the patient condition, and on the other hand, the one currently available investigation means presents extremely high rates of toxic risk. Hence, the attempt, however incompletely successful, at carrying out clinic surveys of a subjective type (manual measurement of certain parameters) or at using alternative investigation instruments (MOIREE chamber) which has characterized the activity of many research teams.

SUMMARY OF THE INVENTION

Accordingly, in the light of the problems encountered with conventional techniques and apparatus for clinic investigation of scoliosis, it is an object of this invention to provide an apparatus enabling postural vices to be documented through a non-invasive and non-ionizing examination easily carried out in clinic practice.

Another object of the invention is to provide such an apparatus which can show results through displays and numbers of direct clinic significance.

A further object of this invention is to provide such an apparatus which can provide functional data not detectable by radiography, and which can be substituted for the latter as a non-toxic instrument of surveying even slight functional alterations, assessing the extent of such alterations and their course (periodic observation of suspect cases), monitoring a patient under therapy (need for frequent investigation), and of functional recovery following incruential therapy or surgical intervention.

It is another object of this invention to provide such an apparatus, which is quite harmless for the patient, simple to use, and adapted to permit repeated examinations at frequent intervals with a high degree of automation and extremely short times.

Still another object of the invention is to provide such an apparatus which enables the operator to more deeply investigate specific cases for diagnostic purposes such as to extend the survey to any particular postures of the subject.

Yet another object of this invention is to provide such an apparatus which can be fabricated from readily available components and be of moderate cost, so as to be within the scope of hospitals as well as of private medical studios, gymnasia for corrective gymnastics, and private diagnosis centers.

According to one aspect of this invention, these and other objects, such as will be apparent hereinafter, are achieved by an apparatus for clinically documenting postural vices, characterized in that it comprises in combination:

(a) a platform adapted to support a subject to be examined;

(b) a plurality of transducers associated with said platform and each adapted to provide at least one component of the force exerted thereon by said subject;

(c) analog-to-digital converter means circuit-wise connected to said transducers and to a number of channels dependent on the number of said force components;

(d) clock generator means functionally interconnected with said analog-to-digital converter means so as to drive its sampling;

(e) TV camera means so positioned as to pick up the image of said subject on said platform and cooperating with monitor means to display said image, said TV camera and said monitor being operatively connected circuit-wise to said clock generator means for driving the raster clocks, so as to sample the rest reaction of said subject on said platform for each image;

(f) a processor unit operatively connected circuit-wise to the output from said analog-to-digital converter means of said clock generator means and driving analog and digital circuitry for directly representing said vector on said monitor;

(g) adder means adapted to add together the signal representative of each image found by the raster clock and the TV signal from said TV camera means so as to provide a present vector overlapping the subject image; and (h) analog and digital circuits for calibrating the force scales and spatial dimensions.

BRIEF DESCRIPTION OF THE DRAWINGS

Further features and advantages of the apparatus for clinically documenting postural vices, according to the invention, will be more readily understood from the following detailed description of an embodiment whereof, as illustrated by way of example and not of limitation in the accompanying drawings, where:

FIGS. 2 to 4 show useful diagrams for a better understanding of the operation of the inventive apparatus.

DESCRIPTION OF THE PREFERRED EMBODIMENTS

Figure 1:
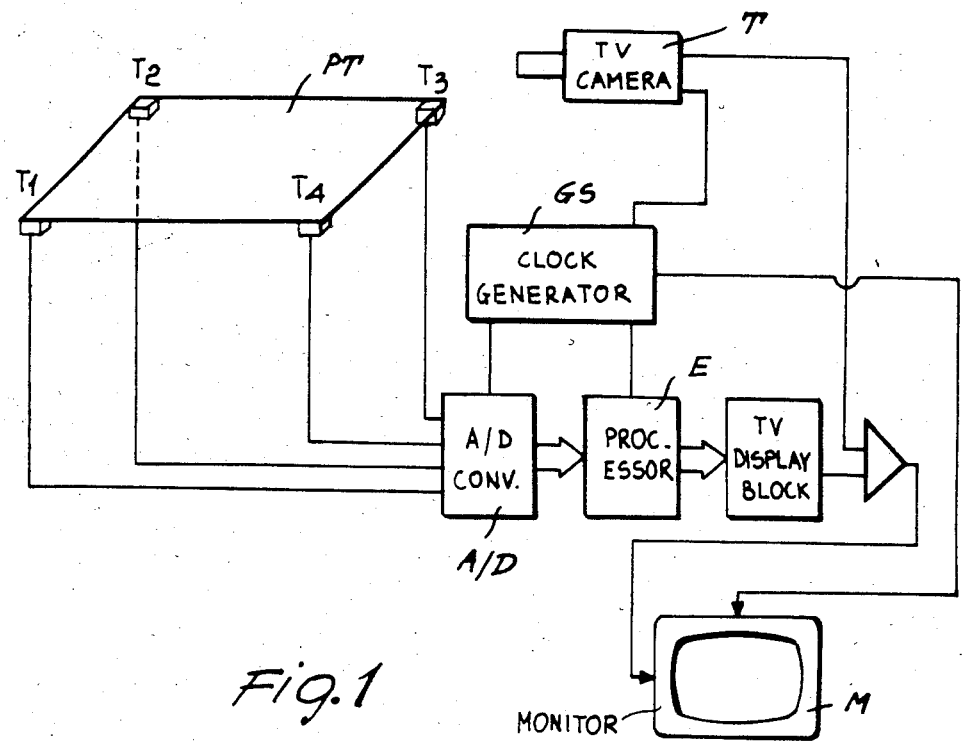
FIG. 1 is a general block diagram of an apparatus according to the invention.

Making reference to the drawing views, and in particular to the block diagram of FIG. 1, an apparatus according to the invention comprises a platform, indicated at PT and of a substantially known type.

Positioned below the platform PT, e.g. at the four corners thereof, are four transducers $T_1, T_2, T_3$ and $T_4$, e.g. of the piezoelectric or strain gage types, being each adapted to provide:

(a) for dynamic analysis purposes, that is where also of interest are the horizontal components, the three components $F_x, F_y$ and $F_z$ of the force acting on each of them.

(b) For static analysis purposes, with the subject motionless on the platform, only the vertical component acting on each of them.

Thus, six signals are generated for case (a) above, namely:

$F_{z1}, F_{z2}, F_{z3}$ and $F_{z4}$ = vertical components on the four transducers;

$F_x = F_{x1}, F_{x2}, F_{x3}$ and $F_{x4}$ = sum of the four horizontal components in the direction X;

$F_y = F_{y1}, F_{y2}, F_{y3}$ and $F_{y4}$ = sum of the four horizontal components in the direction y;

For case (b) above, the following four signals are adequate:

$F_{z1}, F_{z2}, F_{z3}$ and $F_{z4}$ = vertical components on the four transducers.

Use of other force platforms with different structures and transducers would involve corresponding changes in the numbers of the inputs and calculation algorithms for the instantaneous point of application of the force and of the three components Fx,Fy and Fz of said force, while the remainder of the apparatus would be left substantially unaltered.

As may be seen, the outputs from the four transducers $T_1, T_2, T_3$ and $T_4$ are input to an analog-to-digital converter, indicated at A/D in FIG. 1, which as the skilled one may appreciate, should have a number of channels equal to the useful inputs which, as mentioned, would be six for case (a) and four for case (b).

Sampling is driven by a clock generator GS, at the frequency of 50 Hz, which also drives the raster clocks for the TV camera and monitor M, thereby the mechanical event or rest reaction of the subject on the platform is sampled for each image.

Of course, the survey may be carried out, either simultaneously or successively, on the three planes X,Y and Z. In the former case, TV cameras should be used, one of which would be located below the plane of the platform PT, which in such a case is made of a transparent material.

The apparatus of this invention includes, as a basic component thereof, a processor E, provided for receiving and processing the rest reaction data from the subject on the platform, through the converter A/D and under control by the clock generator GS. In particular, the processor is arranged to control a circuit block of TV representation of the rest reactions from the subject on the platform to reveal scoliotic affections of the subject. More particularly, the following representations are provided.

Representation of the plane Y

Assuming that the TV display is decomposed into I horizontal rows or lines, each of which identifies with $i = 1, 2, 3, \ldots I$.

Let Ts be the raster or frame time; then, the scanning time will be for each row:

$$T_L = \frac{T_s}{I}$$

Let each horizontal row or line be discretized into K k-th intervals (pixels), each with a duration time $$t = \frac{T_L}{K}$$

The entire TV display is identified by a $I \times K$ pixel matrix, where I is the number of rows and K the number of columns (see FIG. 3).

$X_a$ = point of application of the vector is calculated as follows: let $X_{1p}$ be the X coordinate of the midpoint between the first transducer pair ($T_1$ and $T_4$ in FIG. 2) and $X_{2p}$ be the X coordinate of the midpoint between the second transducer pair ($T_2$ and $T_3$ in FIG. 2), then $X_{1p}$ and $X_{2p}$ will be found with a process of spatial calibration consisting of overlapping two moving pointers (blank spots) appearing on the screen on the preset line i(P) on the spatial markers marked directly on the platform.

This calibration will define the spatial scale through the expressions, $$k(X_{1p}) = t(X_{1p})/\Delta t$$

$$k(X_{2p}) = t(X_{2p})/\Delta t$$

where, $k(X_{1p})$ and $k(X_{2p})$ are the pixels at the markers at $X_{1p}$ and $X_{2p}$, respectively;

$t(X_{1p})$ and $t(X_{2p})$ are the times on the line i(P) whereat the pointers overlapping $X_{1p}$ and $X_{2p}$, respectively, appear.

Figure 2:
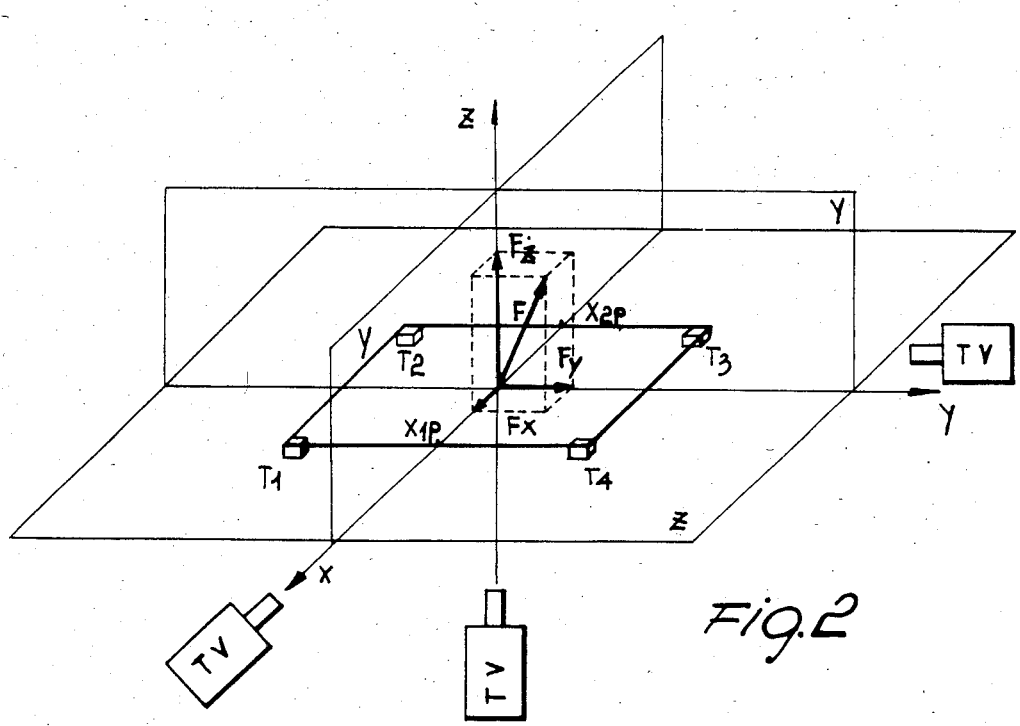

The value $k(X_a)$ the thickness of the plate over the transducers being negligible is calculated as (FIG. 2).

$$k(X_a) = \frac{(F_{z2} + F_{z3})}{F_z} [k(x_{2p}) - k(x_{1p})] + K(X_{1p})$$

Thus the pixel at the lower end of the vector will be given by i(P), $k(X_a)$.

Identifying the scale of vertical forces as $N_i$ = (number of rows per Volt) and that of the horizontal forces as $N_k$ (number of k-th intervals per Volt), the upper vector end will be $$i(Z_s) = i(p) + N_1 \cdot (F_{Z1} + F_{Z2} + F_{Z3} + F_{Z4})$$

and $$k(X_s) = K(X_A) = N_k \cdot (F_x).$$

Simple trigonometric calculations will then locate all the pixels forming the entire vector.

Representation on a TV display

For each image found or spotted by the raster clock a signal is formed which when added to the TV signal from the TV camera gives the vector overlapping the subject image.

This signal will be null before the row counter reaches $i(Z_s)$ and column counter reaches $k(X_s)$ (upper end of the vector). On this occurrence, the output signal has a pulse of duration $\Delta t$ and such an amplitude as to provide the blank on the monitor.

That same pulse will be formed for all the rows with $i(Z_s) \leq i \leq i(P_a)$ at the k-th columns calculated as previously indicated.

Representation on the plane X

The same processing as previously described applies, except that X is replaced with Y.

Representation on the plane Z

Two representation types are possible:
(a) Parametrized trajectory or path of the point of application according to the diagram of FIG. 4A. In this case, for each image a point is represented having coordinates $X_a$ and $Y_a$ calculated as previously described; on the plane Z where the four fixed points forming the vertices of a rectangle represent the four transducers of the platform (spatial reference).
(b) In each image, a vector beginning from the point $(X_a, Y_a)$ is represented with components $F_x$ and $F_y$ calculated as previously described.

According to a further aspect of the invention, it is also possible to store in a dedicated memory the data relating to the force vectors, thus enabling:
(a) reviewing of the mechanical phenomenon (evolution with time of the force vectors on the various planes) at a natural rate, slowed rate, in succesion with manual control;
(b) reviewing of the space-time representation of the evolution of the vectors on the various planes in a single image wherein all the vectors which followed one another during the phenomenon are stored.

For clinic analysis, the subject is merely required to stay on the platform PT in front of the TV camera T after the doctor, to facilitate readout, has placed at some significant reference spots (spinal processes at the level of the seventh cervical and first sacral of the apex of the bend on the sternum, on the iliac crests and great trocanthers) simple self-adhesive markers.

In particular, the survey is effected at five levels, namely: front frontal view; rear frontal view; right side view; left side view; rest plane. Signal processings provide directly on the monitor M the subject image overlapped by the vertical line conducted through the barycenter (VB). For the analysis, the operator will position a moving pointer, which appears on the screen, on the above-specified reference points. The apparatus will provide a series of numbers which quantify the following magnitudes:

misalignment of the spine relatively to VB at the level of the seventh cervical (VCC);
misalignment of the spine relatively to VB at the sacral level (DCS);
distance VB-apex of the bend (DAC);
pelvic asymmetry (AP) on the front plane;
pelvis rotation (DB);
load asymmetry (AC).

Also obtained for each of the five levels considered is the photography of the image on a monitor.

The entities thus obtained are of very important clinic significance.

In fact, misalignment of CV, pelvic asymmetry, and pelvis rotation are characters already regarded as of import to the diagnosis and prognosis of idiopathic scoliosis, even though the difficulty and inaccuracy with which they are currently spotted has always made them difficult to utilize clinically. They are usually spotted or detected by manually processing the radiographic plates, without significant spatial or postural references, or by means of direct measurements on the patient which are of necessity approximative.

The AC, although regarded as important in the detection of the disease, cannot be spotted on a clinic basis.

In particular, as mentioned hereinabove, while the radiographic display retains unreplaceable information as relates to the structure of the rachis (serious cases and pre-operatory investigation), the survey provided by the apparatus according to the invention is to be regarded as complementary to and substitutive of radiography.

To evaluate the effectiveness of the survey performed with the apparatus of this invention, a first trial prototype has been used as formed by assembling available devices and simply optically mixing the TV displays to produce preliminary surveys on a sample group of scoliotic subjects (20 subjects).

Tests carried out have unequivocably evidenced the interest of the data to be derived for diagnoses, documentation and monitoring of scoliosis. In particular, the possibility of quantifying the following has been ascertained:

misalignment for C.V. with respect to the barycenter axis;
pelvis rotation;
asymmetry of load distribution;
variation of said parameters in different scoliotic subjects and during treatment, e.g. with corsets.

It may be appreciated from the foregoing that the apparatus according to the invention fully achieves its objects.

In particular, an apparatus has been provided which permits, through a non-invasive examination, easily carried out in clinic practice, documenting of postural vices and the assessment of the loads on the various articulations, e.g. of an athlete while practicing a sport. The results are obtained by means of images and numbers of direct clinic significance, as already usually considered in clinic practice.

While the invention has been described with reference to a presently preferred embodiment thereof, it should be born in mind that it is susceptible to many changes and modifications without departing from the scope of the inventive concept as defined, in particular, in the appended claims.

I claim:
1. An apparatus for clinically documenting postural vices, comprising in combination:
a platform;
a plurality of transducers arranged in proximity of said platform and measuring three mutually perpendicular components of the force exerted thereon by a subject to be examined carried on said platform, said transducers generating each an electric signal proportional to the vertical component of said force and two electric signals proportional to the resultants of the horizontal and vertical components, respectively, of said force;
clock generator means;

analog-to-digital converter means circuit-wise connected to said transducers and to said clock generator means so as to receive from said transducers said electric signals periodically at sampling times;

TV camera means arranged in proximity to said platform and circuit-wise connected to said clock generator means so as to pick up the image of said subject on said platform synchronously with said electric signals;

a processor unit circuit-wise connected to the output of said analog-to-digital converter means, said processor unit generating vectors representative of the resultants of the forces exerted by the subject on said platform calculating the application points of said vectors and driving analog and digital circuitry for directly representing said vectors;

adder means circuit-wise connected to said TV camera means and said analog and digital circuitry for adding together said vectors and said picked up image; and monitor means circuit-wise connected to said adder means and said clock generator means for selectively displaying said vectors as overlapping the picked up image and said application points.

2. An apparatus according to claim 1, wherein said analog-to-digital converter means have six input lines.

3. An apparatus according to claim 1, wherein said TV camera means includes a single TV camera for successively surveying three mutually perpendicular planes.

4. An apparatus according to claim 1, wherein said TV camera means comprises three TV camera for simultaneously surveying three mutually perpendicular planes.

5. An apparatus according to claim 1, wherein said processor unit comprises analog and digital circuits carrying out calibration of the scales for the forces and spatial dimensions.

6. An apparatus according to claim 1, further comprising videorecording still camera means providing photographies or records of images displayed on said monitor means.

* * * * *